United States Patent

Strandberg, Jr. et al.

[11] Patent Number: 5,149,981
[45] Date of Patent: Sep. 22, 1992

[54] METHOD FOR MONITORING SIZE ENCAPSULATION OF YARN BY DETERMINING HAIRINESS OF THE YARN

[76] Inventors: Charles F. Strandberg, Jr., 202 Longview Rd., High Point, N.C. 27260; Robert C. Strandberg, 1718 Aftonshire Dr., Greensboro, N.C. 27410

[21] Appl. No.: 723,752

[22] Filed: Jul. 1, 1991

Related U.S. Application Data

[63] Continuation of Ser. No. 472,114, Jan. 30, 1990, Pat. No. 5,043,590, which is a continuation-in-part of Ser. No. 428,992, Oct. 30, 1989, Pat. No. 5,072,691.

[51] Int. Cl.$^5$ ............................................. G01N 21/86
[52] U.S. Cl. ...................................... 250/571; 28/183
[58] Field of Search ............... 250/571, 572, 562, 563; 356/429, 430, 238; 28/178, 183; 118/712; 427/8, 10

[56] References Cited

U.S. PATENT DOCUMENTS

| | | | |
|---|---|---|---|
| 3,044,345 | 7/1962 | Schottler | 88/14 |
| 3,582,661 | 6/1971 | Pijls | 250/219 |
| 4,634,280 | 1/1987 | Paulson, Jr. | 356/385 |
| 4,710,396 | 12/1987 | Seydel et al. | 427/8 |
| 4,717,870 | 1/1988 | Vuncannon | 324/65 R |
| 4,738,866 | 4/1988 | Conklin et al. | 427/10 |
| 4,793,035 | 12/1988 | Nehrenberg et al. | 28/183 |
| 4,812,043 | 3/1989 | Vanstaen | 356/385 |
| 4,948,260 | 8/1990 | Felix et al. | 356/429 |

FOREIGN PATENT DOCUMENTS 0226843 11/1986 Fed. Rep. of Germany.
0274649 7/1988 Fed. Rep. of Germany.

OTHER PUBLICATIONS

"Yarn Hairiness" by A. Barella in *Textile Progress*, vol. 13, No. 1, 1983, pp. 50-53.
"Yarn Evenness" The Textile Institute, *Textile Progress*, vol. 14, No. 3/4, 1986, pp. 26-29.

*Primary Examiner*—David C. Nelms

[57] ABSTRACT

A method for quantifying size encapsulation of yarn on a slasher comprising measuring the hairiness of yarn entering a slasher prior to the application of size to the yarn, measuring the hairiness of the yarn leaving the slasher and solving the equation:

$$\text{Size Encapsulation} = 360\left(1 - \frac{\text{Hairs at Delivery}}{\text{Hairs at Entry}}\right) \text{degrees.}$$

Apparatus for quantifying the size encapsulation of yarn on a slasher comprises an entry hairiness sensor positioned at the entry side of a slasher, a delivery hairiness sensor positioned at the delivery side of the slasher, the entry and delivery sensors producing signals proportional to the hairiness of the yarn at the entry and delivery sides of the slasher respectively, and a computer for solving the above indicated equation and producing an output signal representative of size encapsulation.

22 Claims, 6 Drawing Sheets

METHOD FOR MONITORING SIZE ENCAPSULATION OF YARN BY DETERMINING HAIRINESS OF THE YARN

This is a continuation of application Ser. No. 07/472,114 filed Jan. 30, 1990, now U.S. Pat. No. 5,043,590 which was a continuation-in-part of pending application Ser. No. 07/428,992 filed Oct. 30, 1989, now U.S. Pat. No. 5,072,691.

BACKGROUND OF THE INVENTION

1. Field of the Invention

The invention relates to a method and apparatus for monitoring size encapsulation of yarn on a slasher.

2. Description of the Prior Art

Size encapsulation is a measure of the degree that a starch or other film covers the surface of the yarn making up a warp preparatory to weaving.

The sizing machine or slasher generally utilizes a hot liquid starch bath into which several thousand individual strands or ends of yarn which make up the warp are immersed. After immersion, excess liquid is squeezed out by passing the warp between tightly compressed squeeze rolls. The warp is then passed over several sets of steam heated drying cylinders which evaporate most of the water. An even dispersion of solid starch is left on the yarn in the form of a coating. The starch penetrates the soft yarn, and this helps to keep it from breaking off. Size encapsulation is expressed in degrees from 0 to 360 as an average measure of coverage around the yarn.

Very fine hairs protrude from the surface of spun yarn before it is sized and one of the main objects of sizing is to bind these hairs to the yarn and to cover both with the smooth size film to protect the bundle of hairs from the abrasive forces of the loom where the warp will be woven into cloth.

After the warp is dried, adjacent ends or strands may be stuck together by excess size. The adjacent ends are separated by pulling them alternately over and under round bars which extend through the entire warp. During this process, some of the size actually covering the hairs breaks off and the hairs once again protrude from the surface of the yarn.

The degree of size encapsulation around each yarn in the warp has always played an important role in reducing loom stops due to warp end breaks. This importance has increased in recent years as a consequence of increasing loom speeds made possible by the use of air instead of a projectile or shuttle to propel the filling yarn through the shed or opening between alternate ends or strands of yarn in the warp.

When numerous hairs protrude from the yarn making up the warp, they impede the air blast and, if sufficiently severe, cause the filling stop motion on the loom to be activated.

This effect was discovered in the mills three years ago, which prompted us to furnish moisture sensors between drying sections on the slasher to assure the optimum amount of moisture in the yarn at the moment it contacts a hot drying cylinder of the final dryer. Our moisture controls are being used now to regulate the steam pressure on the first dryers to achieve this objective.

SUMMARY OF THE INVENTION

In connection with this effort to maximize the degree of size encapsulation, we have developed a means of monitoring it on the slasher while the warp is being sized. Not only can the effect of moisture in the warp between drying sections upon size encapsulation be observed and maximized during processing, but other variables can also be adjusted to maximize size encapsulation. These include the moisture in the yarn, the temperature of the liquid size, the temperatures of the drying cylinders, squeeze roll pressure, and tension in the yarn as adjacent ends are separated.

The means to maximize encapsulation consists of two photoelectric optical sensors which convert the passage of hairs on the yarn to a proportional voltage. One of the sensors is used on one sample yarn at the entry into the sizing process and one is used on a sample yarn at the delivery end of the process.

Since the hairs protrude outward when parts of the size film are lost, the number of hairs remaining compared with the number of hairs on the unsized yarn is a measure of the lack of degree of size encapsulation. Therefore, $$\text{Size Encapsulation} = 360\left(1 - \frac{\text{Hairs at Delivery}}{\text{Hairs at Entry}}\right) \text{degrees.}$$

Since the warp is stretched by varying percentages depending upon fiber makeup, each unit of yarn length at entry is stretched to a correspondingly longer length at delivery. No compensation for stretch is necessary, because the output voltage from the sensors is proportional to the number of hairs passing through the sensors per unit of time. By this means, the number of hairs on a unit length of yarn at entry is compared with the number of hairs on the same unit length stretched at delivery.

DESCRIPTION OF THE PREFERRED EMBODIMENTS AND OBJECTS OF THE INVENTION

The invention relates to a method and apparatus for quantifying size encapsulation of yarn on a slasher by sensing the hairiness of the yarn at the entry end of the slasher, prior to sizing the yarn, and again sensing the hairiness of the yarn at the delivery end of the slasher and solving the equation:

$$\text{Size Encapsulation} = 360\left(1 - \frac{\text{Hairs at Delivery}}{\text{Hairs at Entry}}\right) \text{degrees.} \quad (1)$$

In a preferred embodiment of the invention the hairiness of the yarn at the entry end and at the delivery end of the slasher is measured by entry and delivery photoelectric sensors which sense the hairs projecting outwardly from the body of the yarn and produce an electrical signal which is proportional to the number of hairs projecting from the yarn. The electrical signals produced by the entry and delivery sensors are fed into a computer which solves equation (1) above.

For a perfectly sized yarn, the yarn will be perfectly encapsulated and no hairs will project outwardly from the yarn. The delivery hairiness sensor will detect zero hairs therefore the solution of equation (1) will result in size encapsulation equal to 360 degrees.

If the slasher would fail to size the yarn, the hairiness of the yarn sensed at entry and at delivery would be equal therefore the solution of equation (1) would result in size encapsulation equal to zero degrees.

Neither of the above mentioned extremes are normal, therefore it is an object of the invention to monitor size encapsulation of yarn on the slasher in order that various controls may be adjusted to optimize the degree of size encapsulation.

It is within the scope of the invention that the electrical signal produced by the entry and delivery hairiness sensors may be an analog signal proportional to yarn hairiness or it may be a signal corresponding to a count of the hairs projecting from the yarn.

One hairiness sensor which is adapted for use in this invention and which is a component of the invention comprises a light source emitting rays of light, such as an incandescent lamp, a solid state LED or a solid state laser diode, first optical means for collecting rays of light from the light source and converging the collected rays of light in a beam toward a focal point, second optical means located on the opposite side of the focal point from the first optical means for collecting the beam of light emerging from the focal point and converging same along a path, the main core of the yarn sample being located beyond the focal point from the first optical means and extending adjacent and transversely to the light beam emerging from the focal point, the main yarn core being substantially contiguous to and outside of the emerging beam so that hairs projecting from the core on the side of the core nearest the emerging beam intersect the emerging beam and produce a variation in light collected by the second optical means which is proportional to the magnitude of yarn hairiness, a photodetector such as a photo diode for high machine speeds or other photoelectric means positioned in the converging path of light from the second optical means for producing an a-c voltage signal which is proportional to the hairiness of the yarn sample, an audio-frequency amplifier or a wide band amplifier (0-1 MHz) which amplifies the a-c voltage signal from the photoelectric means, an amplifier-based full wave or other suitable rectifier connected to the amplifier which rectifies the amplified a-c voltage signal, an output load resistor, and a potentiometer having a resistor connected in series with the rectifier, the potentiometer having an adjustable tap which is connected in series with the output load resistor for adjusting the d-c voltage across the load resistor to any desired value that is proportional to yarn hairiness.

Figure 6:
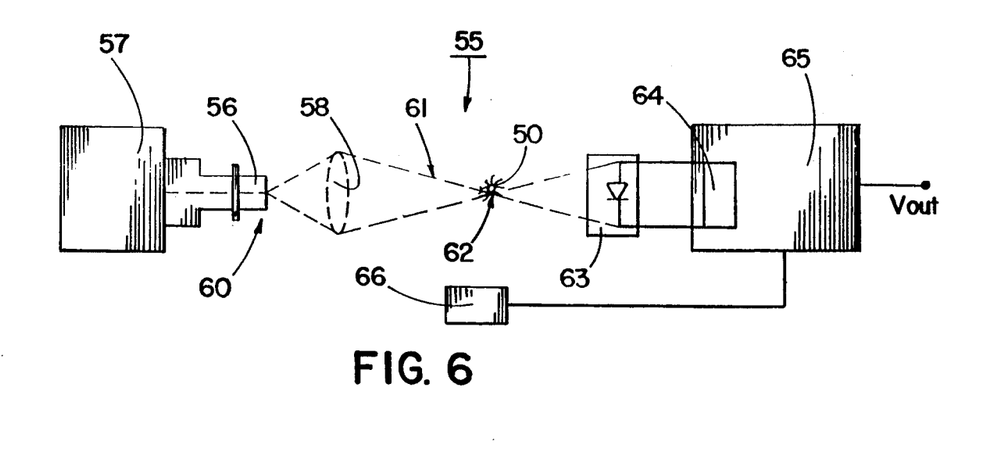
FIG. 6 depicts another embodiment of the yarn hairiness sensor.

The preferred form of the yarn hairiness sensor is shown in FIG. 6 whereby a laser diode, a power supply and a focusing lens comprises the light source. The laser beam is focused to a narrow point and enlarges therebeyond to converge upon a photodetector. The resultant photo current is amplified by a wide band amplifier and is converted to a voltage proportional to yarn hairiness by a conditioning circuit and by a signal encoder.

The preferred method of the invention comprises monitoring size encapsulation of yarn by counting protruding hairs from yarn for a selected yarn length. The count is input to a digital-to-analog convertor for a fixed time interval whereby the analog voltage output is proportional to the hair count. By comparing a reference count to a test count, size encapsulation can be easily monitored.

With the foregoing objects and features in view and such other objects and features as may become apparent as this specification proceeds the invention will be understood from the following description taken in conjunction with the accompanying drawings wherein like characters of reference are generally used to designate like parts.

DETAILED DESCRIPTION OF THE DRAWINGS AND OPERATION OF THE INVENTION

Figure 1:
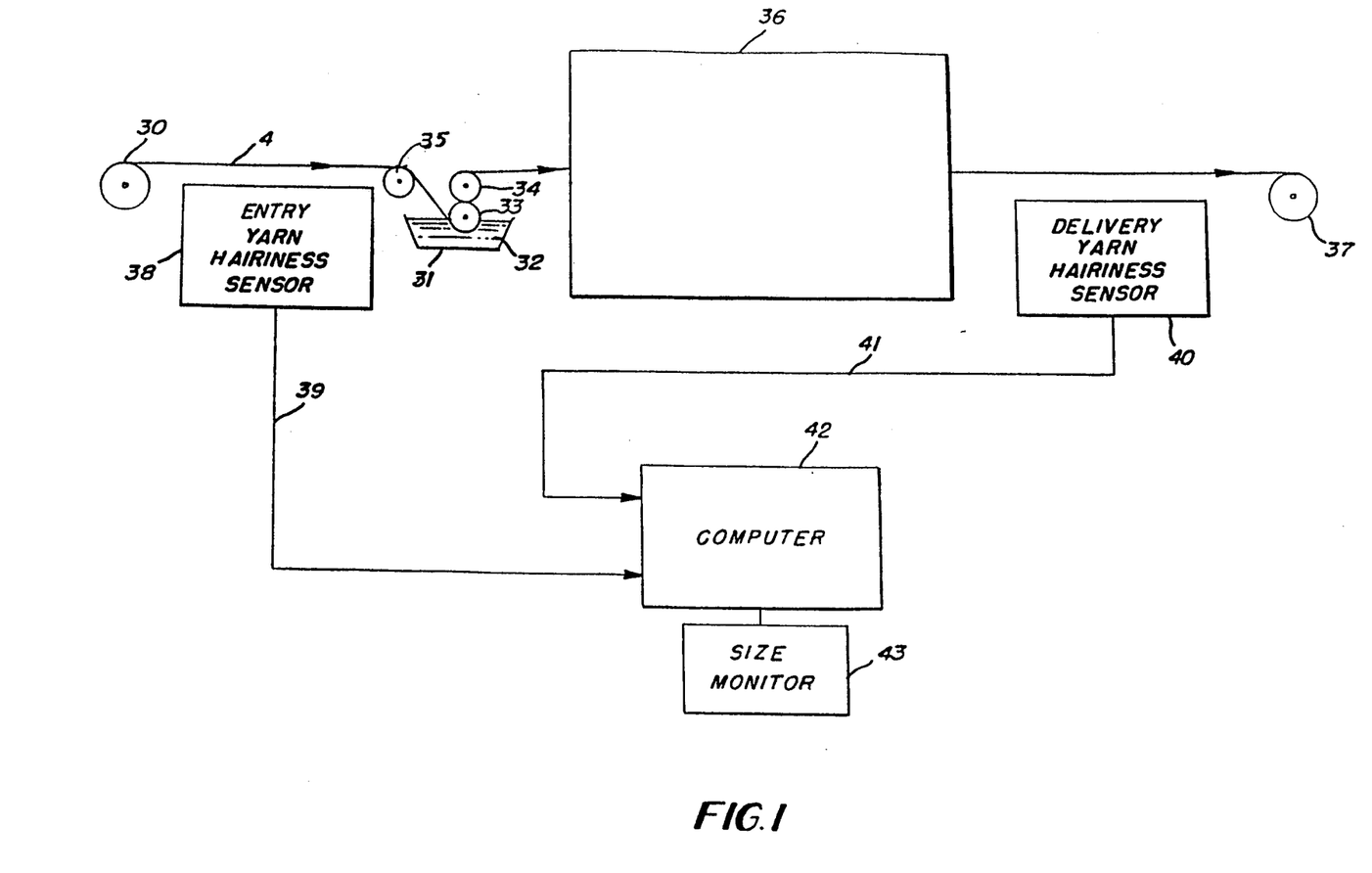
FIG. 1 is a simplified diagram of a typical slasher equipped with the invention.

FIG. 1 shows a diagramatic view of a simplified typical slasher equipped with the present invention. A warp beam 30 supplies a sheet of warp threads 4 over a guide roll 35 to a size box 31 which is supplied with liquid size 32 to a predetermined level. In the size box 31 the warp threads 4 are passed under the bottom of squeeze roll 33 and then are passed between the upper roll 34 and the bottom roll 33 where pressure is applied to squeeze excess size from warp threads 4. The warp threads 4 then pass from the upper squeeze roll 34 onto the drying cylinders (not shown) of a drying section 36 to evaporate the water from the liquid size solution to a desired moisture content. The dried warp threads 4 upon leaving the dryer section 36 passes to the loom beam 37 where they are wound upon the loom beam.

There are many variations of the simplified typical slasher illustrated in FIG. 1 in present use. Most slashers include condition sensors of various kinds for controlling the pressure exerted by the squeeze rolls 33 and 34, for controlling the temperature of the drying cylinders (not shown) in the drying section 36 and for controlling the speed and tension of the warp sheet traveling through the slasher, to mention only some of the known controls used in connection with slashers in current use.

It is not the intent to limit the use of the size encapsulation monitor of the present invention to use with the simplified typical slasher illustrated in FIG. 1, since the size encapsulation monitor may be used in conjunction with slashers of various makes to monitor the degree of size encapsulation of the yarn as it leaves the slasher.

The size encapsulation monitor of the present invention includes an entry yarn hairiness sensor 38 located between the warp beam 30 and the size box 31 and a delivery yarn hairiness sensor 40 located at the delivery side of the drying section 36 near the loom beam 37.

Electric signals generated by the entry and delivery yarn hairiness sensors are supplied over lines 39 and 41 respectively to computer 42 which solves the equation:

$$\text{Size Encapsulation} = 360\left(1 - \frac{\text{Hairs at Delivery}}{\text{Hairs at Entry}}\right) \text{degrees.}$$

Size encapsulation in degrees is displayed on the size monitor display 43.

Figure 3:
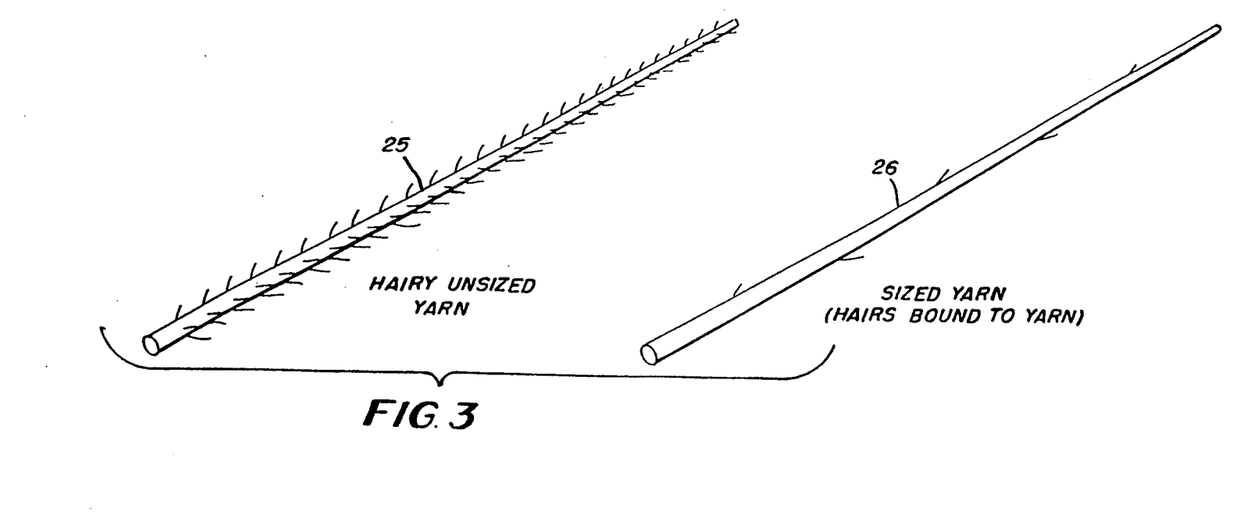
FIG. 3 is a perspective view showing a comparison of the hairiness of unsized and sized yarn.

FIG. 3 illustrates a section 25 of a hairy unsized yarn and a section 26 of a sized yarn which has the hairs bound to the yarn by the size. Even though sizing encapsulates many of the hairs present in unsized yarn, there will still be some hairs protruding from the yarn when the yarn leaves the drying section 36. Various controls may be actuated in response to the size encapsulation signal produced by the computer 42 in order to maintain the maximum possible degree of size encapsulation.

Figure 2:
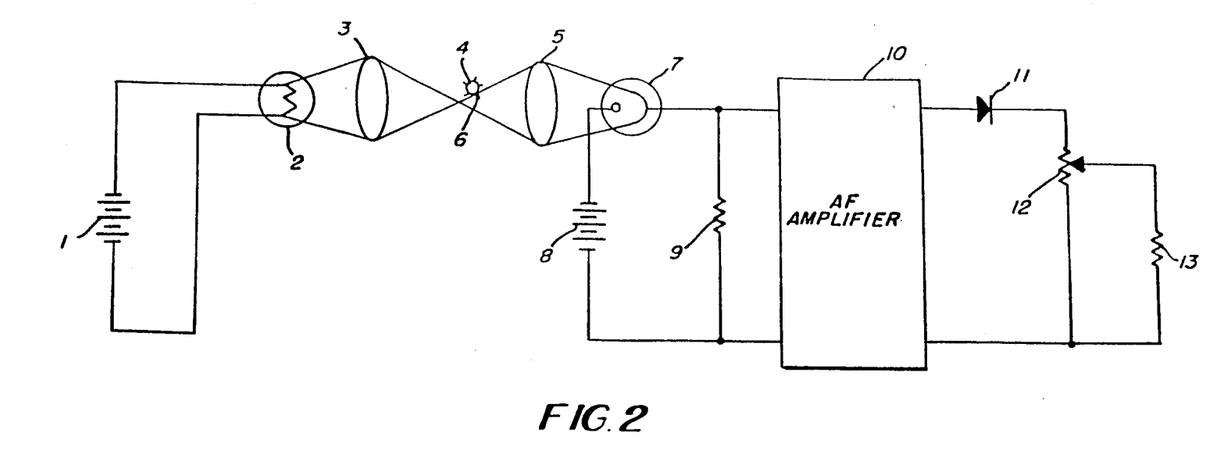
FIG. 2 is a schematic diagram of one of the yarn hairiness sensors used in the invention showing photo electric and optical sensing means.

A yarn hairiness sensor found to be suitable for the entry and delivery yarn sensors 38 and 40 shown in FIG. 1 is illustrated in FIG. 2. The light source 2 contains a spring-wound filament and is powered by a pure d-c source 1. One sample of wrap thread 4 is located immediately outside the narrow slit of light 6 which is before its focal point at the position of the yarn. This location for the sample yarn keeps it outside the field of view but keeps its hair protrusions in the field of view.

The magnitude of yarn hairiness produces a proportional variation in the light projected on the photo diode 7, thus causing its conductance to vary accordingly. This a-c voltage, proportional to yarn hairiness, is developed across a load resistor 9, which is connected to the input of a conventional audio-frequency amplifier 10. After amplification, the resultant proportional voltage is rectified by rectifier 11 and applied across a potentiometer 12 which is used to adjust the output voltage to any desired value that is proportional to yarn hairiness. Power supply 8 is connected to photo diode 7 and resistor 13 is seen in FIG. 2 joined to potentiometer 12.

While the above described hairiness sensor was developed by us and is a component of the present invention, it is not intended that the invention be limited to the use of the hairiness sensor illustrated in FIG. 2 since other hairiness sensors may be substituted.

Figure 4:
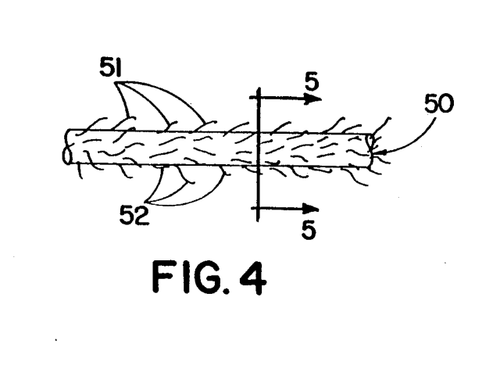
FIG. 4 illustrates a side elevational view of a single yarn end.
Figure 5:
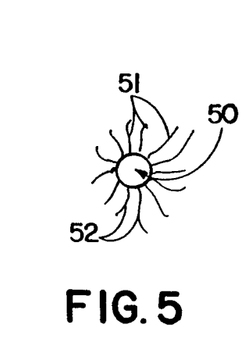
FIG. 5 shows the yarn end of FIG. 4 along lines 5—5.

FIGS. 4 and 5 show a typical yarn end view from both the side (FIG. 4) and end-on (FIG. 5). Various hairs 51 and 52 protrude from yarn body 50 randomly. The closer you get to yarn body 50, the larger the number of hairs 51 and 52 are observable.

FIG. 6 is a simplified schematic of another yarn hairiness sensor 55. A laser diode 56, power supply 57, and focusing lens 58 constitute light source 60 for sensor 55. The inclusion of laser diode 56 assures compact size, long life, and reliable operation. However, incandescent lamps or infrared LEDs could be used with some compromise in performance. But, considering the low cost of laser diode 56 coupled with a lifetime greater than 10 years and the ability to focus the laser diode beam to micro-size spots clearly underlines the laser advantages of laser diode 56. Beam 61 is focused to a small spot 62 and yarn 50 is guided immediately outside narrow focus point or spot 62 perpendicular to laser beam 61. Beam 61 enlarges beyond this focal point and impinges onto a photodetector 63. The resultant photocurrent is amplified by a high-gain, wide-band amplifier 64 and converted into a voltage proportional to yarn hairiness per unit length by schematic signal conditioning circuit 65 and speed encoder 66.

Figure 7:
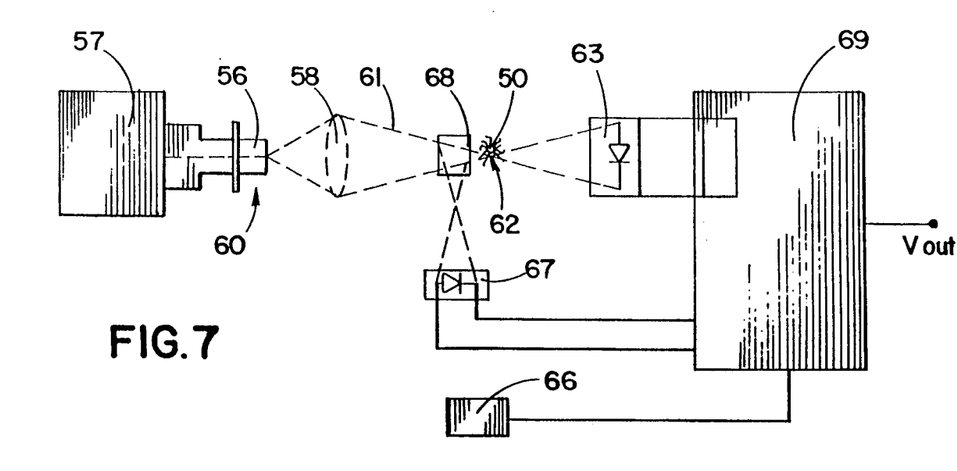
FIG. 7 pictures yet a third embodiment of the yarn hairiness sensor.

The apparatus shown in FIG. 7 is similar to that shown in FIG. 6 with the addition of a second photodetector 67 to provide automatic compensation against variations in light intensity from aging or from ambient temperature changes. A beam splitter 68 divides laser diode 56 output and, in addition to illuminating the yarn, it also presents a reference amount of light from laser diode 56 to photodetector 67. Within the signal processing circuitry, shown schematically at 69 the reference voltage output from photodetector 67 is subtracted from the varying voltage output from photodector 63. Any variations in the laser light intensity are compensated for automatically.

Figure 8:
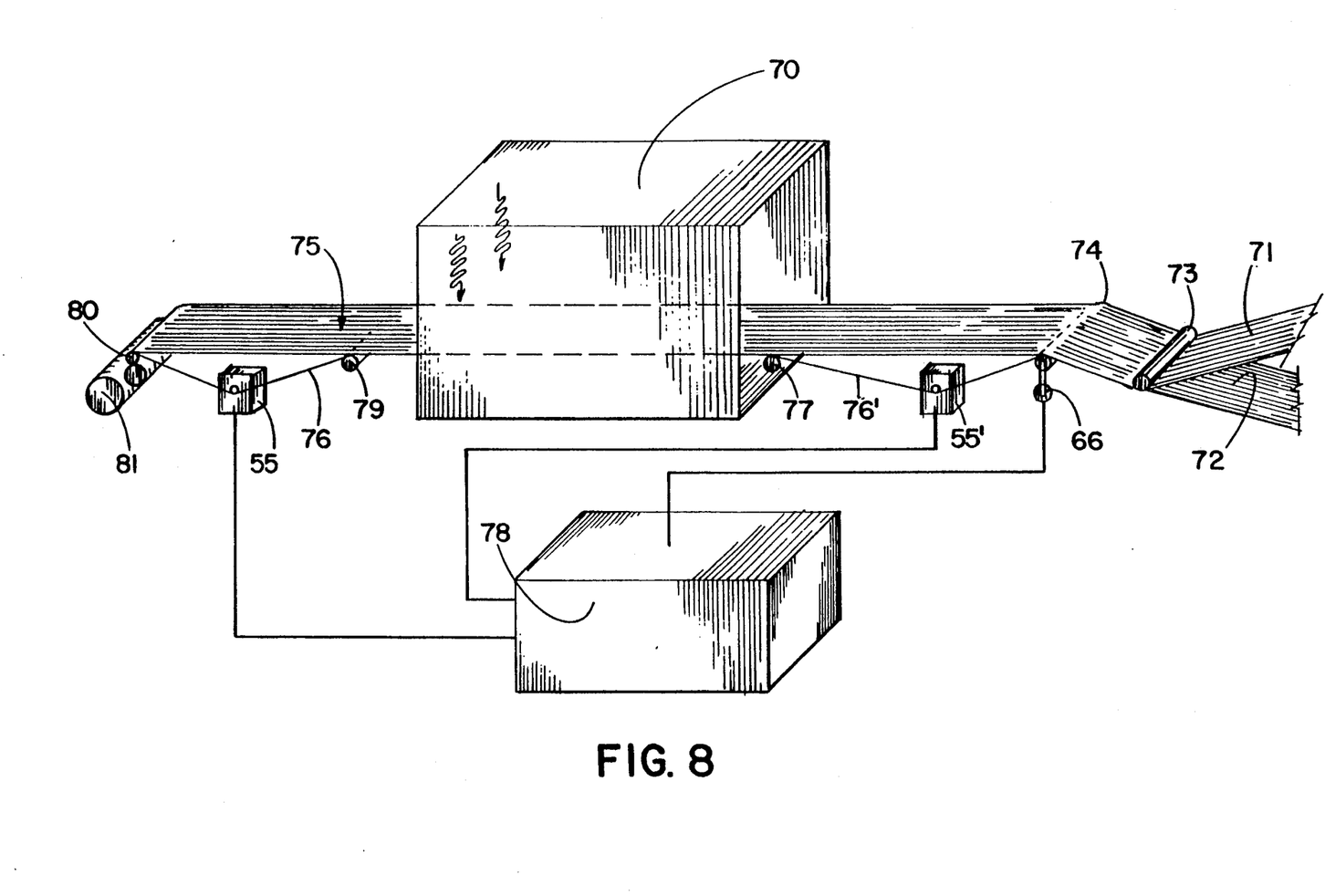
FIG. 8 features another typical slasher utilizing another embodiment of the invention as compared to FIG. 1.

FIG. 8 is a perspective view of schematic slasher 70 equipped with sensors 55 and 55'. Here, different warp sheets 71 and 72 are combined and conveyed by rolls 73, 74 and 77 into slasher 70. After emerging from drying, warp 75 passes on and is conveyed by rolls 79 and 80 to the take-up or loom beam 81. Yarn hairiness sensors 55 and 55' are employed to sense a sample yarn 76, 76' at both the entering end (by sensor 55') and the delivery end (by sensor 55). Also, speed encoder 66 is connected to guide roll 74 for yarn length-based measurements. For time-based measurements, encoder 66 would be omitted and a time-based signal would be generated either within sensors 55, 55' within computer 78.

Figure 9:
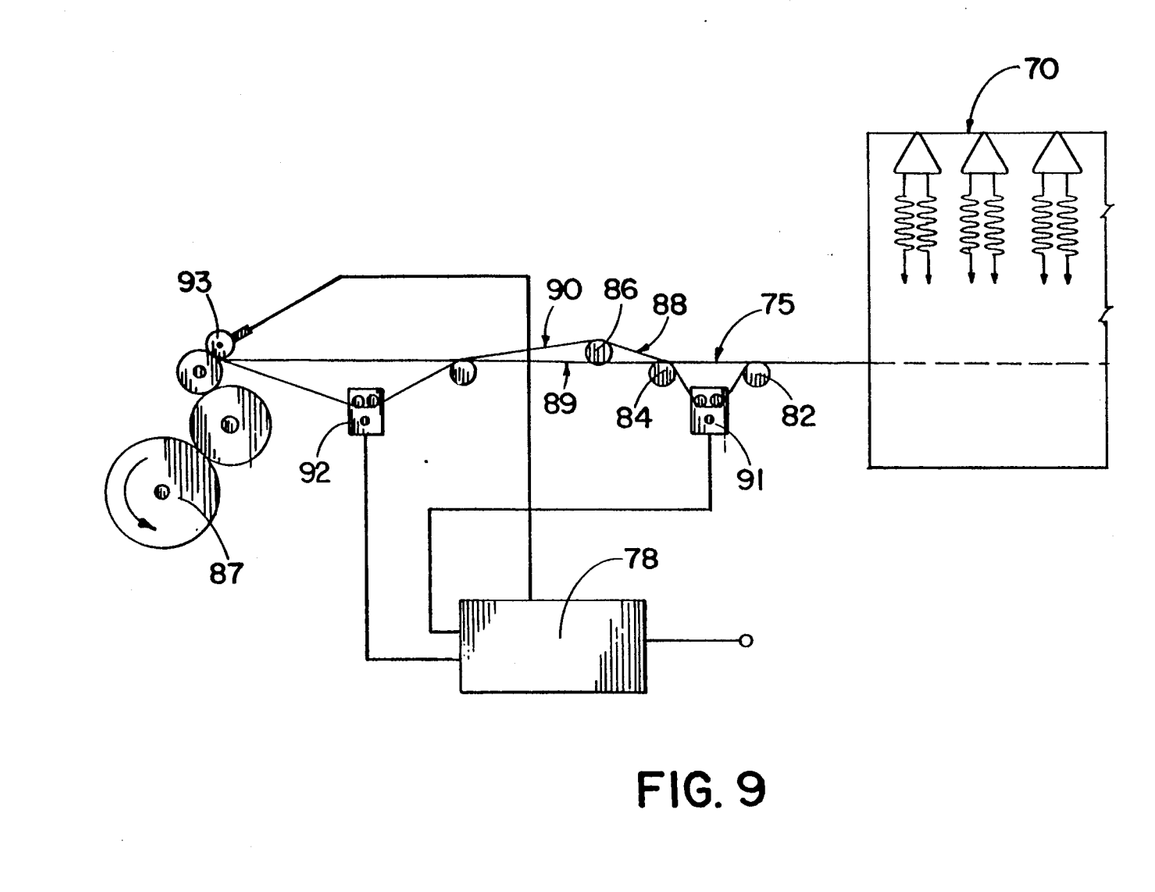
FIG. 9 shows the leasing section of the slasher as seen in FIG. 8 utilizing an embodiment of the invention herein.

FIG. 9 shows the sensor applied to the leasing section at the delivery end of slasher 70. Here warp 75 is guided over typical rolls 82 and 84 prior to first lease rod 86. The warp is intentionally divided above and below lease rod 86 to insure that yarn ends adhered together are separated before being wound onto loom beam 87. As the ends separate immediately before lease rod 86, they do so at a certain "bust angle" 88. The separated ends in separate sheets 89 and 90 are ultimately rejoined just prior to wind up on loom beam 87. Only one lease rod (86) is shown here to avoid confusion, but, in reality, many separate lease rods are employed depending on the total number of ends in warp 75. One yarn hairiness sensor 91 is employed immediately before lease rod 86 before any yarn end separation occurs. A second sensor 92 is employed after all separation has occurred. An encoder 93 is shown for yarn length-based measurements. Again, the encoder would be omitted in time-based measurements. In order to calculate the value of size encapsulation it is necessary, by definition, to employ two yarn hairiness sensors, one located at a first position and one located at a second position relative to the warp yarn movement. However, it should be noted that only one yarn hairiness sensor is required to obtain a relative value for optimizing size encapsulation. Variations in the output of the sensor is a direct indication of variations in size encapsulation and it definitely provides a measure of change in size encapsulation.

Figures 10, 11:
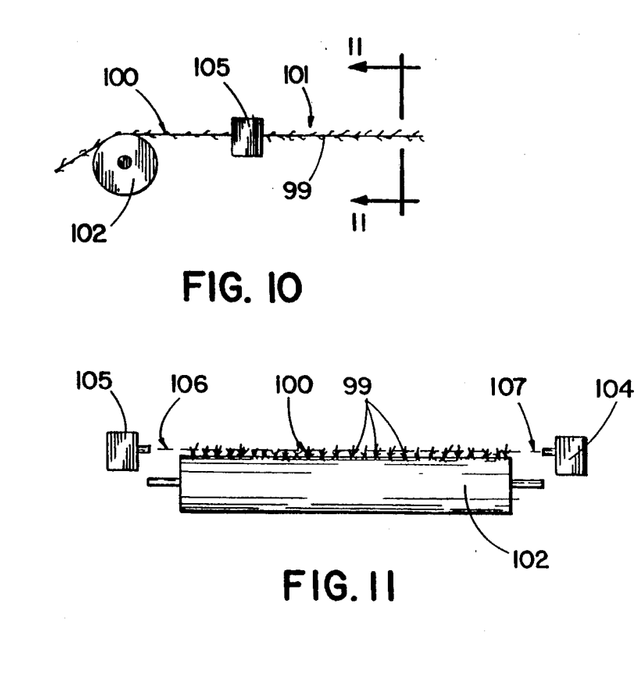
FIG. 10 demonstrates a typical slasher warp with one embodiment of the invention including a laser diode and a photodetector.
FIG. 11 illustrates the apparatus of FIG. 10 along lines 11—11.
Figure 12:
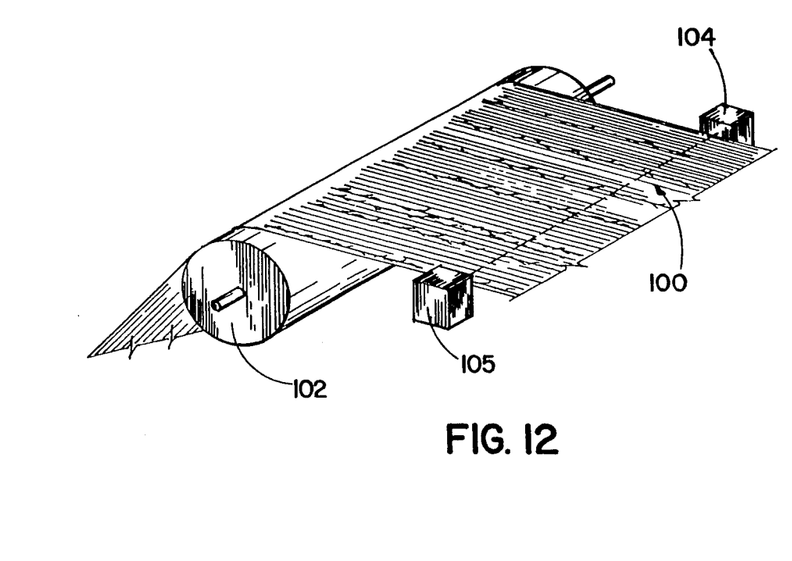
FIG. 12 shows the apparatus of FIG. 11 in perspective fashion.

FIGS. 10, 11 and 12 show warp sheet 100 in side, end and perspective view. A multiplicity of hairs 99 form a generally hairy field 101, to a much lesser extent but similar to carpet pile or towel knap. The more hairs 99 that are present on average, the more dense hairy field 101 and subsequently the greater the attenuation of light in a plane parallel to and close to the plane of warp 100. A well collimated laser diode 105 is employed to direct a small collimated beam 106 across warp 100 onto a sensitive photodetector 104. The location of the line of the laser diode 105 and photodetector 104 is chosen close to a guide roll 102. Guide roll 102 must be well machined to keep run-out to an acceptable minimum thereby ensuring that the warp 100 will not fluctuate up and down as guide roll 102 turns. Such fluctuations would introduce a periodic motion that may be a source error. The laser radiation or beam 107 that reaches photodetector 104 will be attenuated by the total yarn hairiness quality of the combined warp. Therefore, total average warp hairiness can be monitored to provide a measure of warp sizing uniformity.

Yarn hairiness is discussed under the title "Yarn Hairiness" by A. Barella in Textile Progress, Vol. 13, No. 1, Copyright 1983 by the Textile Institute. Various methods and apparatus for the determination of hairiness are discussed by A. Barella on pages 2-14 of the aforesaid publication.

An apparatus for counting loose fiber ends that may exist on textile threads after spinning is disclosed in U.S. Pat. No. 3,044,345, issued Jul. 17, 1962 to Helmut Schottler.

One yarn hairiness monitor presently in commercial use is the Shirley Yarn Hairiness Meter described on page 8 and illustrated on page 9 of Textile Progress, Vol. 13, No. 1.

Whether the yarn hairiness sensor utilizied in the system illustrated in FIG. 1 of the drawing is of the type which produces an analog output signal proportional to yarn hairiness or whether it is of the type which produces a digital output signal representative of a count of the fiber ends projecting outwardly from the yarn counted over some useful length of the yarn is not a limiting factor with respect to the system shown in FIG. 1 since both types of hairiness sensors may be used.

When the hairs are actually counted over a useful length of yarn at entry, they must be counted over the stretched length at delivery. This can be achieved by the use of a tachometer at entry to gate the hairs sensed at entry and delivery to their respective counters.

The term "hairiness" as used in the specification and claims of this patent application refers to the number of loose fiber ends or loops protruding outwardly from a yarn strand over a useful length of the yarn. The loose fiber ends or loops will project from any direction throughout the 360 degree circumference of the yarn. While a useful sampling of the hairiness of the yarn may be taken from only one side of the yarn, as is done by the hairiness sensor shown in FIG. 2, greater accuracy may be obtained by the use of multiple light beams and photocells arranged about the circumference of the yarn so that the hairs projecting in all directions from the yarn may be incuded in the measurement. The sensor would then have means (not shown) for combining the signals from each of the photocells to produce a combined signal proportional to the hairs projecting from the entire 360° circumference of the yarn.

A feature of this invention is that the delivery yarn sensor 40 as seen in FIG. 1 may be mounted on a slide bar or other support for movement transverely to the warp sheet as it is being wound on the loom beam. By moving the delivery yarn sensor 40 back and forth transversely with respect to the warp threads, the evenness of size encapsulation of the yarn threads across the entire warp sheet may be tested. The selected thread is removed from the sensor and another thread is chosen at each position of the sensor along the warp sheet. An alternative to the one transversely movable sensor at delivery can be the use of two or more fixed sensors at delivery. The advantage would be to continuously monitor the uniformity of size encapsulation across the warp to determine malfunctions in the sizing process, such as loss of uniformity of squeeze roll pressure across the warp, or other related problems as they occur. By using one or more sensors at delivery and none at entry the degree of size encapsulation can be monitored in terms of optimization of encapsulation and not in actual degree of coverage. Uniformity of encapsulation is influenced by the amount of moisture in the warp between drying sections, the temperature of the liquid size, the temperature of the drying cylinders, squeeze roll pressure applied and the amount of tension in the yarn as adjacent ends are separated. It is also believed that yarn tension during immersion in the liquid size also affects encapsulation. Additionally, there is an advantage in separately monitoring the loss in size encapsulation which results fom separating the adjacent ends in the leasing section. Tension in this section is currently selected by observation of the angle the adjacent yarns make when they depart to pass alternately over and under the lease rods. The preferred angle is determined by the operator from experience. Tension in the section would be controlled automatically for the least loss of size encapsulation to provide more uniform yarn for weaving and subsequent operations.

The term slasher as used herein is a term commonly used by the textile industry in the United States with respect to textile sizing machines. In Europe and in some other areas the textile industry more commonly applies the term sizing machine with respect to the same apparatus to which the term slasher is applied in the United States. It is not intended by the use of the term slasher in this application to distinguish from the same apparatus known elsewhere as a sizing machine.

The illustrations and examples provided herein are for explanatory purposes and are not intended to limit the scope of the appended claims.

We claim:

1. A method for quantifying size encapsulation of yarn on a slasher comprising the steps of:
   a. measuring the hairiness of yarn at the entry of a slasher prior to the application of size to the yarn,
   b. measuring the hairiness of yarn at delivery from the slasher, and
   c. solving the equation:

$$\text{Size Encapsulation} = 360 \left( 1 - \frac{\text{Hairiness at Delivery}}{\text{Hairiness at Entry}} \right) \text{degrees.}$$

2. A method for monitoring size encapsulation of yarn on a slasher comprising the steps of:
   a. feeding unsized yarn from a yarn supply through a sizing means which applies size to the yarn,
   b. measuring the hairiness of the unsized yarn as it moves from the yarn supply at the entry of the sizing means and producing an electric signal which is proportional to the hairiness of the unsized yarn,
   c. drying the sized yarn after it is delivered from the sizing means, d. measuring the hairiness of the sized yarn after it is dried and producing an electric signal proportional to the hairiness of the sized yarn, e. feeding the electrical signals from steps b and d into a computer and solving the equation:

$$\text{Size Encapsulation} = 360 \left(1 - \frac{\text{Hairiness at Delivery}}{\text{Hairiness at Entry}}\right) \text{degrees}.$$

3. The method of claim 2 including the additional step of:

f. displaying the value of size encapsulation resulting from the solution of the equation set forth in step (e).

4. The method of claim 2 wherein the computer utilized in step (e) produces an electrical output signal representative of the value of size encapsulation resulting from a solution of the equation set forth in step (e) with the additional step of:

f. utilizing the electrical output signal representative of the value of size encapsulation to control the operation of the slasher to optimize the degree of size encapsulation.

5. A method for determining size encapsulation of yarn comprising the steps of:

a. measuring the hairiness of unsized yarn prior to the entry in a means to size yarn, b. feeding the unsized yarn through said sizing means, c. applying size to the yarn, and d. measuring the hairiness of the sized yarn at delivery from said sizing means.

6. The method of claim 5 wherein measuring the hairiness of the unsized yarn comprises the step of producing an electrical signal proportional to the unsized yarn.

7. The method of claim 5 wherein measuring the hairiness of the sized yarn comprises the step of producing an electrical signal proportional to the sized yarn.

8. The method of claim 5 and including the step of computing size encapsulation of the yarn after the step of measuring the hairiness of the sized yarn.

9. The method of claim 8 wherein computing size encapsulation comprises solving the equation:

$$\text{Size Encapsulation} = 360 \left(1 - \frac{\text{Hairiness at Delivery}}{\text{Hairiness at Entry}}\right) \text{degrees}.$$

10. A method for quantifying size encapsulation of yarn utilization a means to size yarn having adjustable controls to optimize the degree of encapsulation, comprising the steps of:

a. sensing the hairiness of yarn at entry of the sizing means, b. sensing the hairiness of yarn at delivery of the sizing means, and c. computing size encapsulation after delivery from the sizing means.

11. The method of claim 10 wherein the step of sensing the hairiness of the yarn at entry comprises optical sensing.

12. The method of claim 10 wherein the step of sensing the hairiness of the yarn at delivery comprises optical sensing.

13. The method of claim 10 wherein the step of computing size encapsulation comprises solving the equation:

$$\text{Size Encapsulation} = 360 \left(1 - \frac{\text{Hairiness after Delivery}}{\text{Hairiness at Entry}}\right) \text{degrees}.$$

14. The method of claim 10 and including the step of adjusting controls of the sizing means to optimize the degree of size encapsulation.

15. A method of monitoring size encapsulation comprising the steps of:

a. sizing a warp of yarn;

b. sensing a sized yarn strand prior to separation of the warp yarns;

c. separating alternate warp yarn strands;

d. rejoining said yarn strands; and e. sensing a delivered yarn strand after rejoining the yarn strands.

16. The method of claim 15 and including the step of solving the equation:

$$\text{Size Encapsulation} = 360 \left(1 - \frac{\text{Hairiness at Delivery}}{\text{Hairiness prior to separation}}\right) \text{degrees}.$$

17. The method of claim 15 wherein the method of sensing a yarn strand prior to separation comprises sensing a yarn strand prior separation by the use of a lease rod.

18. The method of claim 15 and including the step of separating alternate warp yarn strands comprising separating yarn strands by passing alternate yarns along the warp over and under a lease rod.

19. The method of claim 15 wherein the step of sensing a yarn strand comprises sensing a yarn strand which has passed by a lease rod and prior to wind up on a loom beam.

20. A method for monitoring optimization of size encapsulation of hairy warp yarns comprising the steps of:

a. continuously sensing the hairiness of yarn at a first position along a warp surface by passing a light beam over the warp for attenuation by yarn hairs;

b. intercepting said attenuated light passing beyond said warp; and c. generating electrical signals proportional to the yarn hairiness sensed.

21. The method of claim 20 and including the step of sensing the hairiness of yarn at a second position along the warp surface.

22. The method of claim 20 and including the step of comparing variations in the generated signals.

* * * * *